United States Patent
Zhao et al.

(10) Patent No.: US 12,254,629 B1
(45) Date of Patent: Mar. 18, 2025

(54) DEEP LEARNING-BASED MRI EXAMINATION AND DIAGNOSIS SYSTEM FOR DISPLACEMENT OF TEMPOROMANDIBULAR JOINT DISC

(71) Applicant: SICHUAN UNIVERSITY, Sichuan (CN)

(72) Inventors: Zhihe Zhao, Sichuan (CN); Wenxin Lu, Sichuan (CN); Yu Li, Sichuan (CN); Lixia Yu, Sichuan (CN); Yanbo Liao, Sichuan (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/782,056

(22) Filed: Jul. 24, 2024

(51) Int. Cl.
  G06T 7/00 (2017.01)
  G16H 50/20 (2018.01)

(52) U.S. Cl.
  CPC ......... G06T 7/0012 (2013.01); G16H 50/20 (2018.01); G06T 2207/10088 (2013.01); G06T 2207/20081 (2013.01); G06T 2207/30008 (2013.01)

(58) Field of Classification Search
  CPC ......... G06T 7/0012; G06T 2207/10088; G06T 2207/20081; G06T 2207/30008; G16H 50/20
  See application file for complete search history.

(56) References Cited

U.S. PATENT DOCUMENTS

| 2013/0204600 A1* | 8/2013 | Mehra | G16H 50/50 |
| | | | 703/11 |
| 2013/0230224 A1* | 9/2013 | Claude | G06T 7/12 |
| | | | 382/173 |

(Continued)

FOREIGN PATENT DOCUMENTS

| CN | 113488161 A | 10/2021 |
| CN | 114399485 A | 4/2022 |

(Continued)

OTHER PUBLICATIONS

1st Office Action of counterpart Chinese Patent Application No. 202311264758.1 issued on Apr. 3, 2024.

(Continued)

*Primary Examiner* — Van D Huynh

(57) ABSTRACT

A deep learning-based MRI examination and diagnosis system for displacement of a temporomandibular joint disc includes: an acquisition unit, configured to acquire a human head MRI image; a labeling unit, configured to obtain temporomandibular joint area images based on the human head MRI image, and label the temporomandibular joint area images to obtain a training set, the temporomandibular joint area images being classified into images in which a joint disc is in normal and abnormal positions in open and closed states; and a diagnosis unit, configured to construct a first temporomandibular joint disc displacement diagnosis model, and train a first jaw joint disc displacement classification model based on the training set to obtain a second (Continued)

temporomandibular joint disc displacement diagnosis model which is configured to classify and recognize temporomandibular joint area images to be diagnosed, and output a temporomandibular joint disc displacement examination and diagnosis result.

7 Claims, 3 Drawing Sheets

(56) References Cited

U.S. PATENT DOCUMENTS

| | | | | |
|---|---|---|---|---|
| 2015/0132716 | A1* | 5/2015 | Kusch | A61C 9/004 433/140 |
| 2016/0249850 | A1* | 9/2016 | Afifi | A61C 9/004 600/407 |
| 2017/0307711 | A1* | 10/2017 | Wundrak | G01R 33/56518 |
| 2020/0268495 | A1* | 8/2020 | Ryakhovsky | A61C 13/34 |
| 2021/0361349 | A1* | 11/2021 | Katzberg | A61B 8/4209 |
| 2021/0365736 | A1* | 11/2021 | Kearney | A61B 6/5294 |
| 2024/0090791 | A1* | 3/2024 | Greiser | A61B 5/055 |

FOREIGN PATENT DOCUMENTS

| | | |
|---|---|---|
| CN | 114400086 A | 4/2022 |
| CN | 116258726 A | 6/2023 |
| KR | 102408452 B1 | 6/2022 |

OTHER PUBLICATIONS

Notice of Allowance of counterpart Chinese Patent Application No. 202311264758.1 issued on May 9, 2024.

* cited by examiner

DEEP LEARNING-BASED MRI EXAMINATION AND DIAGNOSIS SYSTEM FOR DISPLACEMENT OF TEMPOROMANDIBULAR JOINT DISC

CROSS REFERENCE TO RELATED APPLICATIONS

The present application claims the benefit of Chinese Patent Application No. 2023112647581 filed on Sep. 26, 2023, the contents of which are incorporated herein by reference in their entirety.

TECHNICAL FIELD

The present invention relates to the field of MRI examination and diagnosis, and specifically to a deep learning-based MRI examination and diagnosis system for displacement of a temporomandibular joint disc.

BACKGROUND

The temporomandibular joint is one of the most complex small joints in the human body. Internal derangement of the temporomandibular joint is the most common oral and maxillofacial disease characterized by abnormalities in the position and integrity of the joint disc, and is closely related to multidisciplinary oral treatment. The purpose of temporomandibular joint examination is to detect and record anatomical and pathological injuries to the joint disc and surrounding tissues that cause clinical symptoms or signs, and to determine treatment plans. Due to its complex movement, small shape, diverse bone structure, and difficulty in clinical imaging, conventional X-rays, tomography, arthrography, CT scans, etc. cannot well display the joint disc and its relationship with surrounding tissue structures.

MRI examination is an important tool for evaluating temporomandibular joint disorders and is of great value especially for the evaluation of the morphology and displacement of the joint disc, and its promotion and application in clinical practice is of great significance. However, the interpretation of MRI examinations of the temporomandibular joint is extremely difficult for non-specialists. Its images present a variety of morphologies due to individual morphological differences, shooting conditions, etc. Doctors first need to select a layer that can be used for disease diagnosis from a plurality of MRI tomograms, and then distinguish the specific anatomical structure on that layer to make an imaging diagnosis.

In order to improve the speed and accuracy of joint disc diagnosis and reduce the burden on doctors, a solution is provided in the prior art. CN 114400086 A provides a deep learning-based auxiliary diagnosis system for anterior displacement of a joint disc, including: an image data preprocessing module, configured to process a diagnostic image; a feature extraction module, configured to train image data by using a neural network to extract features; a training module, configured to train and update parameter weights of the neural network, and save the weight with the highest accuracy; and a diagnosis module, configured to input joint disc images, classify same, and obtain a diagnosis result. The system can provide auxiliary diagnosis for anterior displacement of a joint disc, but training images of the system do not distinguish between the open and closed states of the mouth, resulting in low accuracy in its diagnosis, or doctors may still need to make a secondary diagnosis for the anterior displacement of the joint disc based on the open and closed states at follow-up.

SUMMARY

An objective of the present invention is to implement MRI examination and diagnosis for displacement of a temporomandibular joint disc in open and closed states.

To achieve the above objective, the present invention provides a deep learning-based MRI examination and diagnosis system for displacement of a temporomandibular joint disc. The system includes:

an acquisition unit, configured to acquire a human head MRI image;

a labeling unit, configured to obtain temporomandibular joint area images based on the human head MRI image, and label the temporomandibular joint area images to obtain a training set, the temporomandibular joint area images being classified into: an image in which a joint disc is in a normal position in an open state, an image in which the joint disc is in anterior displacement in the open state, an image in which the joint disc is in the normal position in a closed state, and an image in which the joint disc is in anterior displacement in the closed state; and a diagnosis unit, configured to construct a first temporomandibular joint disc displacement diagnosis model, and train a first jaw joint disc displacement classification model based on the training set to obtain a second temporomandibular joint disc displacement diagnosis model, the second temporomandibular joint disc displacement diagnosis model being configured to classify and recognize temporomandibular joint area images to be diagnosed, and output a temporomandibular joint disc displacement examination and diagnosis result.

The temporomandibular joint consists mainly of the articular tubercle, the joint disc, and the condyle. Whether the joint disc is displaced anteriorly needs to be judged in combination with its relative positions with the articular tubercle and the condyle. In the open and closed states, the relative positions of the joint disc with the articular tubercle and the condyle are different. Therefore, the traditional auxiliary diagnosis system for anterior displacement of a joint disc does not distinguish between the open and closed states of the mouth in training images, resulting in low accuracy in its diagnosis, and doctors still need to make a secondary diagnosis for the anterior displacement of the joint disc in combination with the open and closed states at follow-up, which cannot truly achieve efficient and accurate MRI examination and diagnosis for displacement of the temporomandibular joint disc in the open and closed states. In this regard, the labeling unit in the present application can classify and label temporomandibular joint area images according to the open and closed states, and the temporomandibular joint area images are classified into: an image in which the joint disc is in a normal position in the open state, an image in which the joint disc is in anterior displacement in the open state, an image in which the joint disc is in the normal position in the closed state, and an image in which the joint disc is in anterior displacement in the closed state. A training set with the joint disc in the normal state and in anterior displacement in the open and closed states can be obtained through the above classification and labeling, and a second temporomandibular joint disc displacement diagnosis model trained with the training set can accurately judge the position of the joint disc regardless of whether the human head MRI image to be diagnosed is in the open or closed state, with no need of doctors to make a secondary judgment.

In some embodiments, the obtaining temporomandibular joint area images based on the human head MRI image specifically includes:

recognizing the joint disc in the human head MRI image, and obtaining the coordinates of the center position of the joint disc and the length of the joint disc in the front-to-back direction of the face;

constructing an area box based on the coordinates of the center position of the joint disc and the length of the joint disc in the front-to-back direction of the face; and extracting temporomandibular joint area images from the human head MRI image based on the area box.

In the existing auxiliary diagnosis system for anterior displacement of a joint disc, images in its training set are obtained by cropping the diagnostic image to retain only the temporomandibular joint disc area. This operation requires professional medical personnel to perform manually since, first of all, it needs to be medical personnel to be able to understand an MRI image, then find the temporomandibular joint disc area from the MRI image, and perform manual cropping. Professional medical personnel are required to operate during cropping since the entire temporomandibular joint needs to be cropped in and other interference information needs to be cropped as little as possible to improve the training efficiency and recognition accuracy of the model. Therefore, this cropping requires professional medical personnel to do a lot of work since if the sample size is small, the training set is insufficient, which will lead to poor model performance, and a large number of samples require a large number of personnel to perform a large number of cropping operations.

In order to solve the problem that traditional systems require professionals to perform cropping in the case of obtaining temporomandibular joint area images, the present application provides a new solution. The applicant's research found that the joint disc has a special shape and is special in the human head structure, and is quite different in the shape from other joints and bones. Therefore, it is only necessary to recognize the joint disc in the human head MRI image. This method can be implemented using image recognition without the participation of professional medical personnel. Further, the applicant's research found that whether it is in the open or closed state, the articular tubercle, the joint disc and the condyle are all located in the same area. Therefore, it is only necessary to construct an area box with the coordinates of the center position of the joint disc and the length of the joint disc in the front-to-back direction of the face, and automatically extract the temporomandibular joint area images from the human head MRI image by using the area box. The entire process from automatic recognition of the articular tubercle to automatic construction of the area box, as well as automatic extraction of the temporomandibular joint area images can be intelligently and automatically implemented. In this way, there is no need for a large number of professional medical personnel to participate in cropping, and preprocessing such as image cropping can be eliminated. A large number of samples can be efficiently obtained by means of the above method, and can be efficiently trained then to obtain an accurate high-performance model.

In some embodiments, the area box is square, the center coordinates of the area box are the coordinates of the center position of the joint disc, and the side length of the area box is twice the length of the joint disc in the front-to-back direction of the face.

The applicant's research found that constructing a square by using the coordinates of the center position of the joint disc as the center coordinates of the area box and using the length twice that of the joint disc in the front-to-back direction of the face as the side length to obtain an area box not only encloses all the articular tubercle, the joint disc and the condyle within the area box, but also does not enclose too much interference information, so that the accuracy and performance of the trained model are better.

In some embodiments, the second temporomandibular joint disc displacement diagnosis model is a YOLO model. The YOLO (You Only Look Once) model is a new object detection model that reconstructs object detection as a single regression problem to be able to predict the bounding box of an object and the probability of each class. Compared with traditional models such as DPMs (Deformable Parts Models) that use a sliding window and R-CNN (Regions with Convolutional Neural Networks) models that need to first propose a potential bounding box and then run a classifier on the bounding box, YOLO uses a single convolutional network to simultaneously predict a plurality of bounding boxes and the class probabilities of these boxes, having the characteristics such as rapidity, the ability to perform global reasoning on images during prediction, and high versatility due to the generalized representation of learnable objects. The output of the second temporomandibular joint disc displacement diagnosis model is the open and closed states and the position of the joint disc.

In some embodiments, two fully connected layers of the second temporomandibular joint disc displacement diagnosis model use randomly initialized weights, and normalize a bounding box of the joint disc as the width or height divided by the width or height of the image, so that the values of both the position and size of the bounding box of the joint disc fall between 0 and 1.

The second temporomandibular joint disc displacement diagnosis model only needs to be marked once and only one model is trained to obtain the prediction of the position (boundary box) and classification (class probability) of a target object (joint disc), having the advantage of easy marking and training.

In some embodiments, an output layer of the second temporomandibular joint disc displacement diagnosis model uses a linear activation function, and the other layers in the second temporomandibular joint disc displacement diagnosis model use a leaky linear rectified function as the activation function, so as to reduce the impact of neuronal death.

The final layer using a linear activation function and the other layers using a leaky linear rectified function as the activation function can reduce the impact of neuron death. The reason is that the death of a neuron node means that the weight parameter of this node will never be updated and this neuron node permanently outputs a value of 0, which is an advantage over the ReLu activation function. According to the update formula of the neural network weight: $w'=w-\alpha\Delta w$ ($\alpha$ is the learning rate), if Relu is used, the output of the relu activation function is 0 when x<0, and its derivative is also 0, which will cause the weight change $\Delta w=0$, and the weight w not be updated.

In some embodiments, the leaky linear rectified function is:

$$\emptyset(x) = \begin{cases} x, & \text{if } x > 0 \\ 0.1x & \text{otherwise} \end{cases}$$

where x refers to the value of the neuron node in this layer of the network, and Ø(x) refers to the final value of the neuron node in this layer of the network after the activation function and serves as an input value of the next layer of the neural network. In this system, using the leaky linear rectified function as the activation function can avoid the death of a neuron node, that is, the case of x<0.

In some embodiments, the loss function of the second temporomandibular joint disc displacement diagnosis model is a loss function composed of a plurality of parts.

In some embodiments, the loss function is:

$$\lambda_{coord} \sum_{i=0}^{S^2} \sum_{j=0}^{B} \mathbb{1}_{ij}^{obj} \left[ (x_i - \hat{x}_i)^2 + (y_i - \hat{y}_i)^2 \right] +$$

$$\lambda_{coord} \sum_{i=0}^{S^2} \sum_{j=0}^{B} \mathbb{1}_{ij}^{obj} \left[ \left(\sqrt{w_i} - \sqrt{\hat{w}_i}\right)^2 + \left(\sqrt{h_i} - \sqrt{\hat{h}_i}\right)^2 \right] + \sum_{i=0}^{S^2} \sum_{j=0}^{B} \mathbb{1}_{ij}^{obj} (C_i - \hat{C}_i)^2 +$$

$$\lambda_{noobj} \sum_{i=0}^{S^2} \sum_{j=0}^{B} \mathbb{1}_{ij}^{noobj} (C_i - \hat{C}_i)^2 + \sum_{i=0}^{S^2} \mathbb{1}_i^{obj} \sum_{c \in classes} (p_i(c) - \hat{p}_i(c))^2$$

where i is the number of a certain grid in a plurality of grids into which the image is divided, j is the number of the bounding box responsible for prediction in the corresponding grid, $x_i$ and $y_i$ are the coordinates of the center of a predicted bounding box relative to the boundary of grid i, $\hat{x}_i$ and $\hat{y}_i$ are the coordinates of the center of a trained bounding box relative to the boundary of grid i, $w_i$ and $h_i$ are respectively the ratios of the width and height of the predicted bounding box to the width and height of the training image, $\hat{w}_i$ and $\hat{h}_i$ are respectively the ratios of the width and height of the trained bounding box to the width and height of the training image, $C_i$ is the class of the predicted bounding box, $\hat{C}_i$ is the class of the trained bounding box, $p_i(c)$ is a conditional confidence score that the predicted bounding box is a certain class, $\hat{p}_i(c)$ is a conditional confidence score that the trained bounding box is a certain class, $\lambda_{coord}$ is a penalty coefficient used to penalize the coordinate difference of the predicted bounding box, S is the grid divided into S×S for the image, and B is the number of predicted bounding boxes in each grid.

Based on the characteristics of this model, since there is only one temporomandibular joint area box in the MRI examination images of the temporomandibular joint and one area box corresponds to merely one image classification, the present invention improves the entropy loss function by removing the calculation of classloss and optimizing the calculation of objectloss, thereby improving the accuracy of the YOLO model for this model.

A complete data set is passed through the neural network multiple times by setting epoch. Epoch is finally set to 50 according to the characteristics of the trained data set and a monitored learning curve, so that the model goes from underfitting to optimal without overfitting.

In some embodiments, the second temporomandibular joint disc displacement diagnosis model uses an Adam W algorithm to update the weight of the model. AdamW is an improvement on the Adam algorithm, which features adaptive learning rates for different gradients and can converge quickly in fewer epochs.

One or more technical solutions provided by the present invention have at least the following technical effects or advantages:

The present invention can implement MRI examination and diagnosis for displacement of a temporomandibular joint disc in open and closed states.

The present invention does not require a large number of professional medical personnel to participate in cropping, preprocessing such as image cropping can be eliminated, and a large number of samples can be efficiently obtained, so that efficient training can be performed to obtain an accurate high-performance model.

In the deep learning-based MRI examination and diagnosis method and system for displacement of a temporomandibular joint disc provided by the present invention, a deep learning model is constructed, and the original MRI examination image of the temporomandibular joint is input into the deep learning model to automatically recognize and extract key areas and classify same, so as to obtain an image recognition result corresponding to the original MRI examination image of the temporomandibular joint.

In the present invention, key areas of an anatomical structure of the temporomandibular joint are marked, a key area box is automatically extracted using a deep learning model, and images in the box are further recognized and classified, so that previous manual work can be automatically completed with no need of preprocessing such as image cropping and with only one deep learning required.

The present invention has the advantages of objectivity, rapidity, good repeatability, etc. Clinicians can assist in determining the position of the temporomandibular joint disc based on image output results and make corresponding clinical diagnoses.

BRIEF DESCRIPTION OF THE DRAWINGS

The accompanying drawings described herein are used to provide a further understanding of the embodiments of the present invention, constitute a part of the present invention, and do not constitute a limitation on the embodiments of the present invention.

In which, 1—articular tubercle, 2—joint disc, 3—condyle.

DETAILED DESCRIPTION

Embodiment 1

Figure 1:
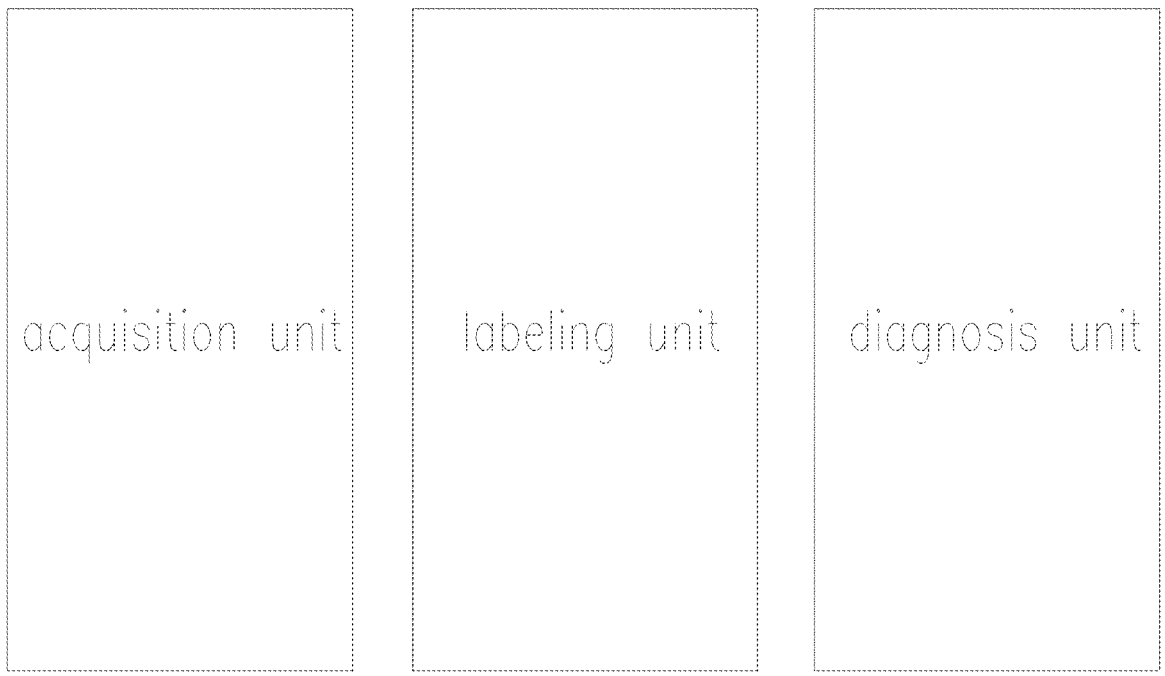
FIG. 1 is a schematic diagram of the composition of a deep learning-based MRI examination and diagnosis system for displacement of a temporomandibular joint disc.

Referring to FIG. 1 that shows a schematic diagram of the composition of a deep learning-based MRI examination and diagnosis system for displacement of a temporomandibular joint disc, the present invention provides a deep learning-based MRI examination and diagnosis system for displacement of a temporomandibular joint disc. The system includes:

an acquisition unit, configured to acquire a human head MRI image;

a labeling unit, configured to obtain temporomandibular joint area images based on the human head MRI image, and label the temporomandibular joint area images to obtain a training set, the temporomandibular joint area images being classified into: an image in which a joint disc is in a normal position in an open state, an image in which the joint disc is in anterior displacement in the open state, an image in which the joint disc is in the normal position in a closed state, and an image in which the joint disc is in anterior displacement in the closed state; and a diagnosis unit, configured to construct a first temporomandibular joint disc displacement diagnosis model, and train a first jaw joint disc displacement classification model based on the training set to obtain a second temporomandibular joint disc displacement diagnosis model, the second temporomandibular joint disc displacement diagnosis model being configured to classify and recognize temporomandibular joint area images to be diagnosed, and output a temporomandibular joint disc displacement examination and diagnosis result.

The acquisition unit may derive MRI images from a nuclear magnetic resonance apparatus and then store the images in a computer for subsequent processing.

Figure 2:
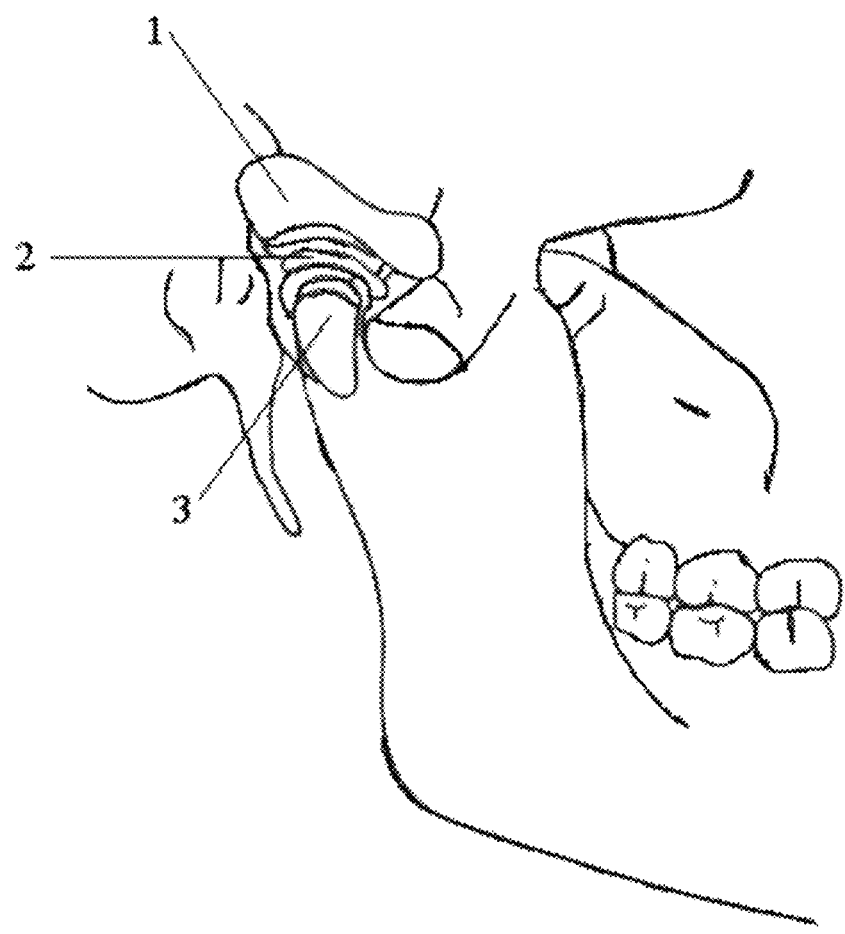
FIG. 2 is a schematic structural diagram of a temporomandibular joint.

Referring to FIG. 2 that shows a schematic structural diagram of a temporomandibular joint, 1 is the articular tubercle, 2 is the joint disc, and 3 is the condyle in FIG. 2. The obtaining temporomandibular joint area images based on the human head MRI image specifically includes:

recognizing the joint disc in the human head MRI image, and obtaining the coordinates of the center position of the joint disc and the length of the joint disc in the front-to-back direction of the face;

constructing an area box based on the coordinates of the center position of the joint disc and the length of the joint disc in the front-to-back direction of the face; and extracting temporomandibular joint area images from the human head MRI image based on the area box.

The recognition of the joint disc can adopt image recognition technology, for example, training a model that can automatically recognize the joint disc.

The joint area box is labeled as follows: the center point of the square area box is first determined by the midpoint of two endpoints of the joint disc in the front-to-back direction of the face, and then a square box with a side length twice the length between the two front and back endpoints of the joint disc is determined by using this point as the center.

The method for acquiring the length of the joint disc in the front-to-back direction of the face is to determine two endpoints of the joint disc in the front-to-back direction of the face based on the recognition of the joint disc, and obtain the length of the joint disc in the front-to-back direction of the face based on the axial length of a line connecting the two endpoints.

Embodiment 1 of the present invention provides a system capable of automatically recognizing MRI images of a temporomandibular joint. The open and closed states of the joint and the position of a joint disc are judged to assist clinicians in diagnosis, shortening the interpretation time, and improving the efficiency and accuracy of interpretation and disease diagnosis.

Figure 3:
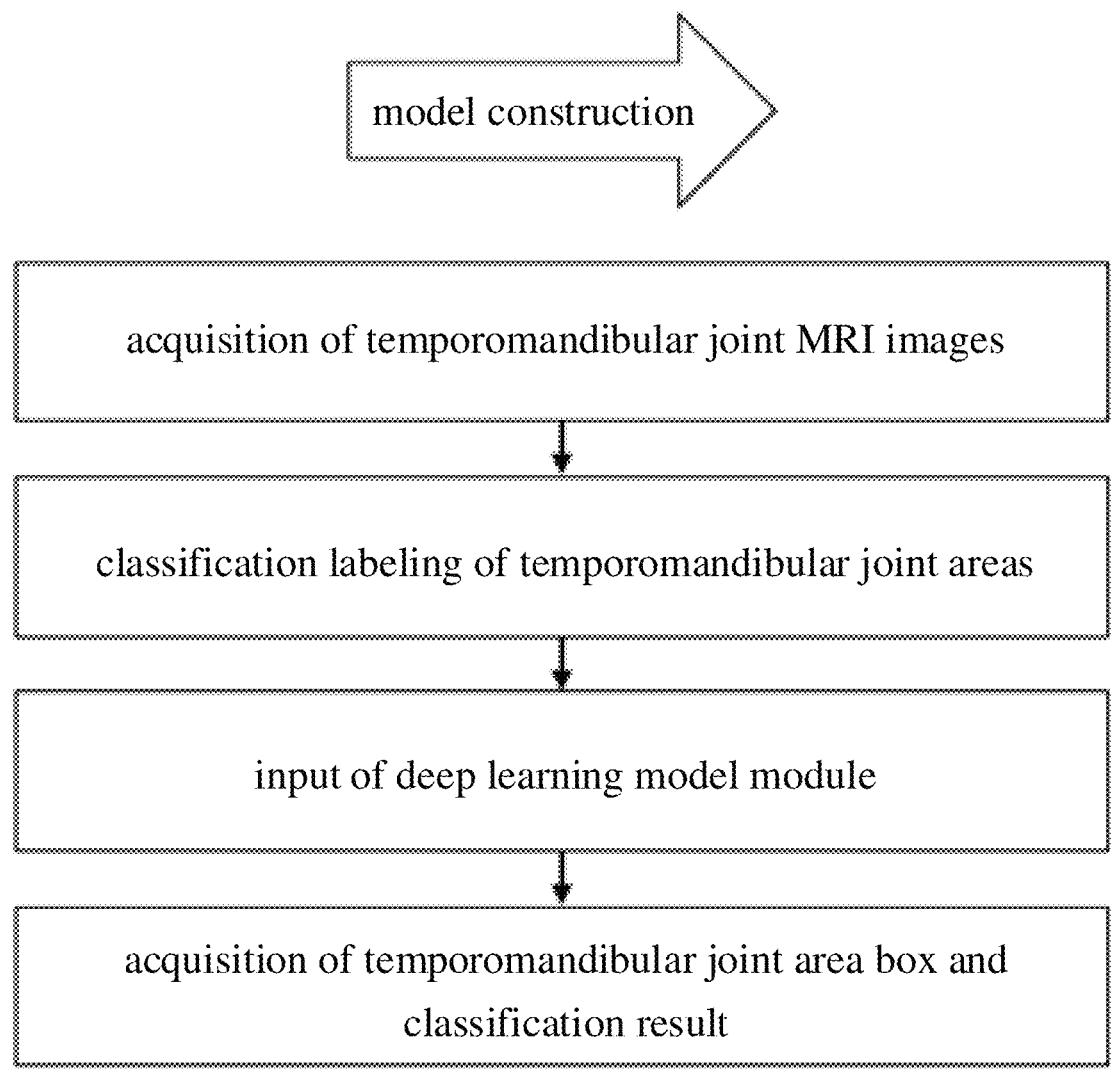
FIG. 3 is a schematic diagram of the construction and workflow of the system.

As shown in FIG. 3 that shows a schematic diagram of the construction and workflow of the system, this embodiment specifically adopts the following technical solution:

MRI examination images of the temporomandibular joint (including images of the joint disc in normal position and anterior displacement in the open and closed states) are acquired to perform classification and labeling on temporomandibular joint areas.

The labeled MRI examination images of the temporomandibular joint are divided into a training set and a validation set.

The images are input into a deep learning model for training and verification, so as to obtain a temporomandibular joint area box and an image classification result of the corresponding MRI examination images of the temporomandibular joint.

The deep learning-based MRI examination and diagnosis system for displacement of a temporomandibular joint disc provided by the present invention includes an acquisition unit, a labeling unit, and a diagnosis unit, specifically implemented in the following manner:

The diagnosis unit is implemented based on a YOLO model of a convolutional neural network.

The determination of the temporomandibular joint area box in the labeling unit is based on the labeling of the temporomandibular joint area. Preprocessing such as image cropping can be eliminated to remove irrelevant information, thereby improving the training efficiency and accuracy of the deep learning model. The temporomandibular joint area is labeled by drawing a square box with a side length twice the length of the joint disc in the front-to-back direction, taking the temporomandibular joint disc structure on the MRI examination images as the center. Key structures in the temporomandibular joint encompassed in this box include the condyle, the joint disc, and the articular tubercle. Under physiological and pathological conditions, the upper and lower parts of the temporomandibular joint disc are the articular tubercle and the condyle, respectively. The anteroposterior diameter of the joint disc is approximately twice the anteroposterior diameter of the condyle, and basically matches the anteroposterior diameter of the posterior slope of the articular tubercle. The condyle may be located directly below, below anteriorly, or below posteriorly to the joint disc, and is connected to the joint disc. Therefore, the box encompasses key structures of the temporomandibular joint while removing irrelevant elements as much as possible.

The labeling unit is based on the classification labeling for the position of the joint disc of the temporomandibular joint in the open and closed states. The classification label is divided into the following categories according to the position of the joint disc in the open and closed states: Category I: normal position of the joint disc in the open state; Category II: anterior displacement of the joint disc in the open state; Category III: normal position of the joint disc in the closed state; Category IV: anterior displacement of the joint disc in the closed state; and Category V: cannot be used for classification.

The temporomandibular joint MRI examination images containing the temporomandibular joint area box and image classification information are input into the initial convolutional layer of the YOLO model to extract training image features, and the open and closed states of output images and the position of the joint disc are predicted through fully connected layers.

The two fully connected layers of the YOLO model use randomly initialized weights, and normalize the bounding box of the object to the width/height divided by the width/ height of the image to make them both fall between (0-1). An output layer of the model uses a linear activation function, and all the other layers use the following leaky linear rectified function (Leaky ReLU) to reduce the impact of neuron death.

The leaky linear rectified function is:

$$\emptyset(x) = \begin{cases} x, & \text{if } x > 0 \\ 0.1x & \text{otherwise} \end{cases}$$

where x refers to the value of the neuron node in this layer of the network, and Ø(x) refers to the final value of the neuron node in this layer of the network after the activation function and serves as an input value of the next layer of the neural network. In this system, using the leaky linear rectified function as the activation function can avoid the death of a neuron node, that is, the case of x<0.

Finally, the following entropy loss function and the AdamW optimization algorithm are used to update the model weights, and finally loss converges:

$$\lambda_{coord} \sum_{i=0}^{S^2} \sum_{j=0}^{B} \mathbf{1}_{ij}^{obj} \left[ (x_i - \hat{x}_i)^2 + (y_i - \hat{y}_i)^2 \right] +$$

$$\lambda_{coord} \sum_{i=0}^{S^2} \sum_{j=0}^{B} \mathbf{1}_{ij}^{obj} \left[ \left( \sqrt{w_i} - \sqrt{\hat{w}_i} \right)^2 + \left( \sqrt{h_i} - \sqrt{\hat{h}_i} \right)^2 \right] + \sum_{i=0}^{S^2} \sum_{j=0}^{B} \mathbf{1}_{ij}^{obj} (C_i - \hat{C}_i)^2 +$$

$$\lambda_{noobj} \sum_{i=0}^{S^2} \sum_{j=0}^{B} \mathbf{1}_{ij}^{noobj} (C_i - \hat{C}_i)^2 + \sum_{i=0}^{S^2} \mathbf{1}_i^{obj} \sum_{c \in classes} (p_i(c) - \hat{p}_i(c))^2$$

where i is the number of a certain grid in a plurality of grids into which the image is divided, j is the number of the bounding box responsible for prediction in the corresponding grid, $x_i$ and $y_i$ are the coordinates of the center of a predicted bounding box relative to the boundary of grid i, $\hat{x}_i$ and $\hat{y}_i$ are the coordinates of the center of a trained bounding box relative to the boundary of grid i, $w_i$ and $h_i$ are respectively the ratios of the width and height of the predicted bounding box to the width and height of the training image, $\hat{w}_i$ and $\hat{h}_i$ are respectively the ratios of the width and height of the trained bounding box to the width and height of the training image, $C_i$ is the class of the predicted bounding box, $\hat{C}_i$ is the class of the trained bounding box, $p_i(c)$ is a conditional confidence score that the predicted bounding box is a certain class, $\hat{p}_i(c)$ is a conditional confidence score that the trained bounding box is a certain class, $\lambda_{coord}$ is a penalty coefficient used to penalize the coordinate difference of the predicted bounding box, S is the grid divided into S×S for the image, and B is the number of predicted bounding boxes in each grid.

Based on the characteristics of this model, since there is only one temporomandibular joint area box in the MRI examination images of the temporomandibular joint and one area box corresponds to merely one image classification, the present invention improves the entropy loss function by removing the calculation of classloss and optimizing the calculation of objectloss, thereby improving the accuracy of the YOLO model for this model.

A complete data set is passed through the neural network multiple times by setting epoch. Epoch is finally set to 50 according to the characteristics of the trained data set and a monitored learning curve, so that the model goes from underfitting to optimal without overfitting.

What is claimed is:

1. A deep learning-based magnetic resonance imaging (MRI) examination and diagnosis system for displacement of a temporomandibular joint disc, characterized in comprising:
   an acquisition unit, configured to acquire a human head MRI image;
   a labeling unit, configured to obtain temporomandibular joint area images based on the human head MRI image, and label the temporomandibular joint area images to obtain a training set, the temporomandibular joint area images being classified into: an image in which a joint disc is in a normal position in an open state, an image in which the joint disc is in anterior displacement in the open state, an image in which the joint disc is in the normal position in a closed state, and an image in which the joint disc is in anterior displacement in the closed state; and
   a diagnosis unit, configured to construct a first temporomandibular joint disc displacement diagnosis model, and train a first jaw joint disc displacement classification model based on the training set to obtain a second temporomandibular joint disc displacement diagnosis model, the second temporomandibular joint disc displacement diagnosis model being configured to classify and recognize temporomandibular joint area images to be diagnosed, and output a temporomandibular joint disc displacement examination and diagnosis result;
   the obtaining temporomandibular joint area images based on the human head MRI image specifically comprises:
   recognizing the joint disc in the human head MRI image, and obtaining coordinates of a center position of the joint disc and a length of the joint disc in a front-to-back direction of a face;
   constructing an area box based on the coordinates of the center position of the joint disc and the length of the joint disc in the front-to-back direction of the face; and
   extracting temporomandibular joint area images from the human head MRI image based on the area box;
   wherein the area box is square, the center coordinates of the area box are the coordinates of the center position of the joint disc, and the side length of the area box is twice the length of the joint disc in the front-to-back direction of the face.

2. The deep learning-based MRI examination and diagnosis system for displacement of a temporomandibular joint disc according to claim 1, characterized in that the second temporomandibular joint disc displacement diagnosis model is a You Only Look Once (YOLO) model, and the output of the second temporomandibular joint disc displacement diagnosis model is the open and closed states and the position of the joint disc.

3. The deep learning-based MRI examination and diagnosis system for displacement of a temporomandibular joint disc according to claim 2, characterized in that two fully connected layers of the second temporomandibular joint disc displacement diagnosis model use randomly initialized weights, and normalize a bounding box of the joint disc as the width or height divided by the width or height of the image, so that the values of both the position and size of the bounding box of the joint disc fall between 0 and 1.

4. The deep learning-based MRI examination and diagnosis system for displacement of a temporomandibular joint disc according to claim 2, characterized in that an output layer of the second temporomandibular joint disc displacement diagnosis model uses a linear activation function, and the other layers in the second temporomandibular joint disc displacement diagnosis model use a leaky linear rectified function as the activation function.

5. The deep learning-based MRI examination and diagnosis system for displacement of a temporomandibular joint disc according to claim 4, characterized in that the leaky linear rectified function is:

$$\emptyset(x) = \begin{cases} x, & \text{if } x > 0 \\ 0.1x & \text{otherwise} \end{cases}$$

wherein $\emptyset(x)$ is the final value of a neuron node in the output layer after the activation function, and x is the value of the neuron node in the output layer.

6. The deep learning-based MRI examination and diagnosis system for displacement of a temporomandibular joint disc according to claim 2, characterized in that the loss function of the second temporomandibular joint disc displacement diagnosis model is a loss function composed of a plurality of parts.

7. The deep learning-based MRI examination and diagnosis system for displacement of a temporomandibular joint disc according to claim 2, characterized in that the second temporomandibular joint disc displacement diagnosis model uses an AdamW algorithm to update the weight of the model.

* * * * *